United States Patent
Feibel et al.

(10) Patent No.: US 9,855,063 B2
(45) Date of Patent: Jan. 2, 2018

(54) SYSTEMS, METHODS, AND APPARATUSES FOR REAMING BONE ELEMENTS

(71) Applicants: Jonathan Feibel, Columbus, OH (US); Robert Gorsline, Columbus, OH (US); Nicholas J. Vallo, New Albany, OH (US); Christos Ragias, New Albany, OH (US); Christopher Brown, Columbus, OH (US); Christopher Hawker, Columbus, OH (US); Jeffrey J. Root, Columbus, OH (US)

(72) Inventors: Jonathan Feibel, Columbus, OH (US); Robert Gorsline, Columbus, OH (US); Nicholas J. Vallo, New Albany, OH (US); Christos Ragias, New Albany, OH (US); Christopher Brown, Columbus, OH (US); Christopher Hawker, Columbus, OH (US); Jeffrey J. Root, Columbus, OH (US)

(*) Notice: Subject to any disclaimer, the term of this patent is extended or adjusted under 35 U.S.C. 154(b) by 255 days.

(21) Appl. No.: 14/194,626

(22) Filed: Feb. 28, 2014

(65) Prior Publication Data

US 2014/0243838 A1 Aug. 28, 2014

Related U.S. Application Data

(60) Provisional application No. 61/770,410, filed on Feb. 28, 2013, provisional application No. 61/912,547, filed on Dec. 5, 2013.

(51) Int. Cl.
*A61B 17/17* (2006.01)
*A61B 17/92* (2006.01)

(52) U.S. Cl.
CPC ........ *A61B 17/1717* (2013.01); *A61B 17/921* (2013.01); *A61B 17/1775* (2016.11)

(58) Field of Classification Search
CPC . A61B 17/17–17/1764; A61B 17/1796; A61B 2017/1771–2017/1792
See application file for complete search history.

(56) References Cited

U.S. PATENT DOCUMENTS 2,486,136 A * 10/1949 Ericsson .............. A61B 17/742
606/67
2,716,406 A * 8/1955 Borella .............. A61B 17/1717
606/104

(Continued)

FOREIGN PATENT DOCUMENTS

CN 201055416 Y 5/2008
DE 20309481 U1 9/2003

(Continued)

OTHER PUBLICATIONS

International Search Report patent application PCT/US2014/019702.

(Continued)

*Primary Examiner* — Christian Sevilla
*Assistant Examiner* — Eric S Gibson
(74) *Attorney, Agent, or Firm* — Benesch, Friedlander, Coplan & Aronoff LLP

(57) ABSTRACT

A stabilization apparatus for reaming bone elements includes an outer sleeve having support rod apertures. Support rods are configured to extend through the support rod apertures and into one or more bone elements to secure the outer sleeve to the bone elements. An inner sleeve is movable axially into the outer sleeve, and rotationally relative to the outer sleeve, when the outer sleeve is secured to the bone elements by the support rods. The apparatus further includes means for releasably blocking movement of the inner sleeve axially out of the outer sleeve, while permitting rotation of the inner sleeve relative to the outer sleeve, when (Continued)

the outer sleeve is secured to the bone elements by the support rods.

14 Claims, 8 Drawing Sheets

(56) References Cited

U.S. PATENT DOCUMENTS

| | | | |
|---|---|---|---|
| 3,171,408 A * | 3/1965 | Childs | A61B 17/17 606/96 |
| 4,237,875 A | 12/1980 | Termanini | |
| 4,381,770 A * | 5/1983 | Neufeld | A61B 17/1721 606/67 |
| 4,621,628 A * | 11/1986 | Brudermann | A61B 17/1707 606/64 |
| 4,696,293 A | 9/1987 | Ciullo | |
| 4,793,363 A * | 12/1988 | Ausherman | A61B 10/025 600/567 |
| 4,917,111 A * | 4/1990 | Pennig | A61B 17/1703 606/97 |
| 4,932,413 A * | 6/1990 | Shockey | A61M 25/0172 600/434 |
| 5,147,367 A * | 9/1992 | Ellis | A61B 17/1728 606/309 |
| 5,324,295 A * | 6/1994 | Shapiro | A61B 17/1714 606/86 R |
| 5,478,343 A * | 12/1995 | Ritter | A61B 17/1725 606/96 |
| 5,601,550 A * | 2/1997 | Esser | A61B 17/1739 606/54 |
| 5,624,447 A * | 4/1997 | Myers | A61B 17/1717 606/104 |
| 5,814,073 A * | 9/1998 | Bonutti | A61B 17/0401 604/14 |
| 5,895,389 A * | 4/1999 | Schenk | A61B 17/17 606/102 |
| 5,904,685 A * | 5/1999 | Walawalkar | A61F 2/0805 606/104 |
| 5,919,192 A | 7/1999 | Shouts | |
| 5,951,561 A * | 9/1999 | Pepper | A61B 17/1717 606/79 |
| 6,033,407 A * | 3/2000 | Behrens | A61B 17/921 606/62 |
| 6,036,657 A * | 3/2000 | Milliman | A61B 10/0266 600/564 |
| 6,036,696 A * | 3/2000 | Lambrecht | A61B 17/1703 606/104 |
| 6,129,729 A * | 10/2000 | Snyder | A61B 17/1725 606/74 |
| 6,162,226 A | 12/2000 | Decarlo, Jr. et al. | |
| 6,200,317 B1 | 3/2001 | Aalsma et al. | |
| 6,224,600 B1 | 5/2001 | Protogirou | |
| 6,231,576 B1 | 5/2001 | Frigg et al. | |
| 6,277,124 B1 | 8/2001 | Haag | |
| 6,355,037 B1 | 3/2002 | Crosslin et al. | |
| 6,371,959 B1 * | 4/2002 | Trice | A61B 17/1725 606/97 |
| 6,419,678 B1 * | 7/2002 | Asfora | A61B 17/1757 606/96 |
| 6,613,065 B2 * | 9/2003 | Lajtai | A61B 17/3417 606/190 |
| 6,638,279 B2 | 10/2003 | Bonutti | |
| 6,656,189 B1 * | 12/2003 | Wilson | A61B 17/1703 606/97 |
| 6,730,087 B1 | 5/2004 | Butsch | |
| 6,761,722 B2 | 7/2004 | Cole et al. | |
| 6,783,530 B1 | 8/2004 | Levy | |
| 6,849,076 B2 | 2/2005 | Blunn et al. | |
| 6,918,910 B2 | 7/2005 | Smith et al. | |
| 7,422,593 B2 | 9/2008 | Cresina et al. | |
| 7,422,594 B2 * | 9/2008 | Zander | A61B 17/17 606/103 |
| 7,749,224 B2 | 7/2010 | Cresina et al. | |
| 7,785,325 B1 | 8/2010 | Milbank | |
| 7,846,164 B2 * | 12/2010 | Castillo | A61B 17/1604 606/184 |
| 7,887,548 B2 * | 2/2011 | Usher, Jr. | A61B 17/1735 606/104 |
| 7,938,832 B2 * | 5/2011 | Culbert | A61B 17/1757 606/103 |
| 7,981,114 B2 * | 7/2011 | Zander | A61B 17/17 604/165.01 |
| 8,007,501 B2 * | 8/2011 | Kaup | A61B 17/1697 606/96 |
| 8,057,472 B2 | 11/2011 | Walker et al. | |
| 8,109,935 B2 | 2/2012 | Stoffel et al. | |
| 8,128,627 B2 | 3/2012 | Justin et al. | |
| 8,317,795 B2 | 11/2012 | Edwards et al. | |
| 8,911,445 B2 * | 12/2014 | Rocci | A61B 17/1686 606/86 R |
| 8,936,600 B2 * | 1/2015 | Soliman | A61B 17/1728 606/102 |
| 9,066,734 B2 * | 6/2015 | Schoenefeld | A61B 17/1757 |
| 9,101,432 B2 * | 8/2015 | Limouze | A61B 17/1725 |
| 9,119,645 B2 * | 9/2015 | McBride | A61B 17/1757 |
| 9,254,126 B2 * | 2/2016 | Frasier | A61B 17/0293 |
| 2003/0004513 A1 * | 1/2003 | Guzman | A61B 17/1635 606/62 |
| 2003/0220641 A1 * | 11/2003 | Thelen | A61B 17/1668 606/60 |
| 2003/0220646 A1 * | 11/2003 | Thelen | A61B 17/1642 606/79 |
| 2004/0215203 A1 | 10/2004 | Michelson | |
| 2005/0070906 A1 | 3/2005 | Clark et al. | |
| 2007/0012816 A1 * | 1/2007 | Kaup | A61B 17/1697 242/615 |
| 2007/0055286 A1 * | 3/2007 | Ralph | A61B 17/1728 606/96 |
| 2008/0255554 A1 | 10/2008 | Richter et al. | |
| 2008/0287951 A1 | 11/2008 | Stoneburner et al. | |
| 2009/0048598 A1 | 2/2009 | Ritchey et al. | |
| 2009/0076555 A1 * | 3/2009 | Lowry | A61B 17/1671 606/280 |
| 2009/0112209 A1 * | 4/2009 | Parrott | A61B 17/1717 606/62 |
| 2009/0216232 A1 | 8/2009 | Buford, III et al. | |
| 2009/0228007 A1 | 9/2009 | Justin et al. | |
| 2009/0275946 A1 * | 11/2009 | Duncan | A61B 17/1725 606/62 |
| 2009/0318927 A1 * | 12/2009 | Martin | A61B 17/1764 606/96 |
| 2010/0087821 A1 | 4/2010 | Trip et al. | |
| 2010/0160913 A1 | 6/2010 | Scaglia | |
| 2010/0331842 A1 | 12/2010 | Milbank | |
| 2011/0060336 A1 | 3/2011 | Pool et al. | |
| 2011/0172662 A1 | 7/2011 | Keilen | |
| 2011/0208188 A1 * | 8/2011 | Mohamed | A61B 17/7233 606/62 |
| 2011/0245830 A1 | 10/2011 | Zgonis et al. | |
| 2011/0282346 A1 | 11/2011 | Pham et al. | |
| 2012/0059376 A1 | 3/2012 | Rains et al. | |
| 2012/0065638 A1 | 3/2012 | Moore | |
| 2012/0123419 A1 | 5/2012 | Purdy et al. | |
| 2012/0197261 A1 * | 8/2012 | Rocci | A61B 17/1686 606/96 |
| 2012/0221005 A1 | 8/2012 | Corneille et al. | |
| 2012/0239038 A1 | 9/2012 | Saravia et al. | |
| 2013/0150858 A1 * | 6/2013 | Primiano | A61B 17/16 606/80 |
| 2013/0172890 A1 * | 7/2013 | Limouze | A61B 17/1725 606/62 |
| 2013/0190570 A1 * | 7/2013 | Hirsch | A61B 17/1697 600/204 |
| 2013/0310886 A1 * | 11/2013 | VanOsten | A61B 17/1717 606/329 |
| 2014/0025078 A1 | 1/2014 | Sidebotham et al. | |

(56) References Cited

U.S. PATENT DOCUMENTS

| 2014/0081281 A1* | 3/2014 | Felder | A61B 17/1717 |
| | | | 606/96 |
| 2014/0243838 A1* | 8/2014 | Feibel | A61B 17/1717 |
| | | | 606/96 |
| 2014/0309648 A1* | 10/2014 | Matityahu | A61B 17/1717 |
| | | | 606/96 |

FOREIGN PATENT DOCUMENTS

| DE | 102008004922 A1 | 7/2009 |
| WO | 9801077 | 1/1998 |
| WO | 9824380 | 6/1998 |
| WO | 2007008177 A1 | 1/2007 |
| WO | 2008116170 A2 | 9/2008 |
| WO | 2008116175 A2 | 9/2008 |
| WO | 2009152270 A1 | 12/2009 |
| WO | 2010140991 A2 | 12/2010 |

OTHER PUBLICATIONS

English machine translation of abstract of DE102008004922A1.
English machine translation of abstract of DE20309481U1.
English machine translation of abstract of CN201055416Y1.
International Search Report and Written Opinion of the International Searching Authority, dated May 28, 2014, from International Pat. App. No. PCT/US2014/019702, international filing date of Feb. 28, 2014.
European Extended Search Report, dated Sep. 26, 2016, from European Pat. App. No. 14757049.3, filed on Feb. 28, 2014.

* cited by examiner

SYSTEMS, METHODS, AND APPARATUSES FOR REAMING BONE ELEMENTS

CROSS-REFERENCE TO RELATED APPLICATIONS

This application claims priority from U.S. Provisional Patent Application No. 61/770,410, filed on Feb. 28, 2013, and U.S. Provisional Patent Application No. 61/912,547, filed on Dec. 5, 2013, each of which is incorporated by reference herein in its entirety.

BACKGROUND

The implantation of orthopedic implanted devices for fusion, stabilization, and fixation of joints, fractures, and other fusions involves various complicated processes and components. The reaming of bone elements for implantation of orthopedic implanted devices often requires an assistant physically stabilizing the bone elements, which may easily lead to shifting and/or misalignment of bone elements during the reaming procedure.

What is needed is a more stable and accurate system, method, and apparatus for reaming bone elements.

SUMMARY

In one embodiment, a stabilization apparatus for reaming bone elements is provided, the stabilization apparatus comprising: an outer sleeve; an inner sleeve; wherein in at least one of the outer sleeve and the inner sleeve include at least one support rod aperture operable to receive and guide a support rod for affixing the stabilization apparatus relative to a bone element.

In another embodiment, a stabilization apparatus for reaming bone elements is provided, the stabilization apparatus comprising: an outer sleeve, the outer sleeve comprising: a soft tissue protection element for operatively protecting soft tissue during a medical procedure and used to guide a reamer, and an outer sleeve handle with at least one interlocking mechanical device to interlock with an inner sleeve handle; and an inner sleeve, the inner sleeve further comprising: a pilot hole guide portion for drilling a pilot hole during a medical procedure.

In another embodiment, a stabilization apparatus for reaming bone elements, the apparatus comprising: an outer sleeve; a bore extending substantially centrally through the outer sleeve; an inner sleeve including a pilot hole guide portion; wherein in at least one of the outer sleeve and the inner sleeve include at least one support rod aperture operable to receive and guide a support rod for affixing the stabilization apparatus relative to a bone element.

BRIEF DESCRIPTION OF THE DRAWINGS

The accompanying figures, which are incorporated in and constitute a part of the specification, illustrate various example apparatuses, systems, and methods, and are used merely to illustrate various example embodiments.

DETAILED DESCRIPTION

Figure 1:
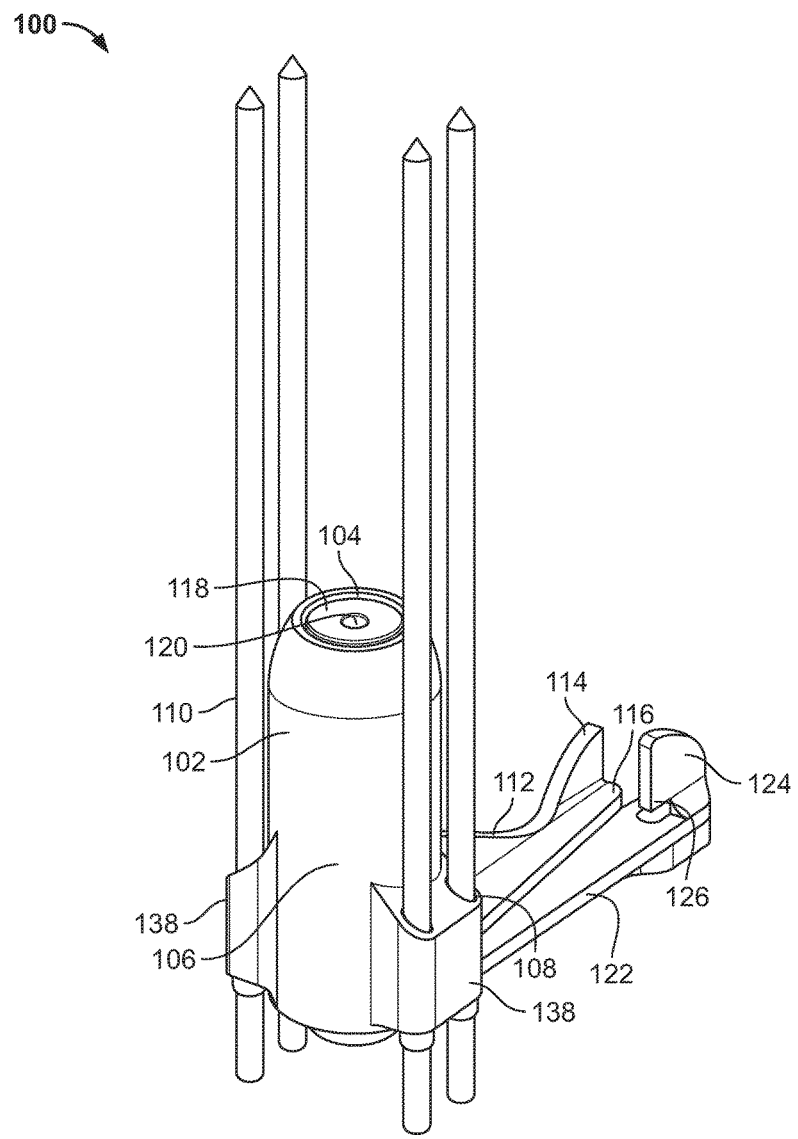
FIG. 1 illustrates an example arrangement of a stabilization apparatus.

FIG. 1 illustrates an example arrangement of a stabilization apparatus 100. Stabilization apparatus 100 may comprise an outer sleeve 102 through which an inner sleeve 104 may extend. Stabilization apparatus 100 may also comprise one or more support rod aperture offsets 138 containing one or more support rod apertures 108 through which support rods 110 may be guided for securing stabilization apparatus 100 prior to, or while, using stabilization apparatus 100 for a medical procedure.

Outer sleeve 102 and inner sleeve 104 of stabilization apparatus 100 may also comprise at least one interlocking mechanical device configured to interlock inner sleeve 104 with outer sleeve 102, which may be an interlocking outer sleeve handle 112 and interlocking inner sleeve handle 122 such that inner sleeve 104 may be selectively secured to outer sleeve 102 when using inner sleeve 104 via interlocking handles 112 and 122.

Stabilization apparatus 100 may be configured to maintain one or more bone elements in a specific desired orientation for reaming a hole through the one or more bone elements. Stabilization apparatus 100 may be configured to maintain one or more bone elements in a specific desired orientation for implantation of an orthopedic implanted device through one or more bone elements. In one embodiment, stabilization apparatus 100 is configured to maintain one or more joints in a specific desired orientation for reaming a hole through the one or more bone elements making up the joint, for insertion of an apparatus for causing compression between bone elements.

Outer sleeve 102 may comprise a substantially cylindrical soft tissue protection element 106 with a series of support rod apertures 108 extending longitudinally through one or more support rod aperture offsets 138 disposed around soft tissue protection element 106. The support rod apertures 108 may permit the passing of any of support rod 110 or like fixation device through outer sleeve 102. Outer sleeve 102 is operable to mate with inner sleeve 104 with pilot hole guide portion 118 of inner sleeve 104 contained within substantially cylindrical soft tissue protection element 106 of outer sleeve 102. Inner sleeve 104 may be contained at least partially within outer sleeve 102.

Inner sleeve 104 may comprise a pilot hole guide portion 118 with a central pilot hole aperture 120. When outer sleeve 102 of stabilization apparatus 100 is substantially fixated by one or more support rods 110 to a body area during a medical procedure, pilot hole guide portion 118 with pilot hole aperture 120 of inner sleeve 104 may be inserted into soft tissue protection element 106 of outer sleeve 102 and rotated such that interlocking outer sleeve handle 112 and interlocking inner sleeve handle 122 are interlocked to prevent at least one of axial, transverse, and rotational movement of inner sleeve 104 relative to the body area during a medical procedure.

Pilot hole guide portion 118 and pilot hole aperture 120 may be used to drill a pilot hole through one or more bone elements. In one embodiment, pilot aperture 120 is used to drill a pilot hole prior to a bone reaming procedure. In another embodiment, the size, shape, and geometry of pilot hole guide portion 118 and pilot hole aperture 120 may vary based on medical procedure, bone size, and location of bone reaming.

Support rod apertures 108 for support rods 110 may be offset to either side of outer sleeve 102 by support rod aperture offsets 138. Size, shape, and geometry of support rod aperture offsets 138 may be varied to vary a location of one or more support rod apertures 108. In one embodiment, support rod apertures 108 are offset according to medical procedure. In another embodiment, support rod apertures 108 are offset according to bone size. In another embodiment, support rod apertures 108 are offset according to bone location. In one embodiment, two or more support rod apertures 108 for support rods 110 may be substantially opposed, and oriented about 180 degrees relative to soft tissue protection element 106. In another embodiment, stabilization apparatus 100 comprises three or more support rod apertures 108 for support rods 110 in which support rod apertures 108 may be substantially evenly distributed about soft tissue protection element 106. That is, three support rod apertures 108 may be oriented about 120 degrees relative to soft tissue protection element 106, while four support rod apertures 108 may be oriented about 90 degrees relative to soft tissue protection element 106, and so on.

In one embodiment, one or more support rods 110 comprise a cutting tip configured to create a channel through bone elements upon rotation of support rods 110. In another embodiment, one or more support rods 110 are configured to be inserted following the drilling of a channel through bone elements with a drill bit. Drilling a channel through bone elements with a drill bit may use support rod apertures 108 as a drilling guide. In another embodiment, one or more support rods 110 comprise a pointed tip configured to create a channel through bone elements upon being driven with an axial force. In one embodiment, support rods 110 may be threaded for drilling into one or more bone elements.

Outer sleeve 102 may use soft tissue protection element 106 to provide protection of soft tissues adjacent to or surrounding the site of bone elements to be reamed. For example, soft tissue protection element 106 may protect at least one of skin, muscle, ligament, cartilage, bone, fat, or any tissue, from contacting or being damaged by a pilot hole drill bit or bone reaming drill bit during use of stabilization apparatus 100. In one embodiment, after pilot hole guide portion 118 and pilot hole aperture 120 are used to drill a pilot hole, inner sleeve 104 may rotated relative to outer sleeve 102 to unlock inner sleeve 104 from outer sleeve 102 such that inner sleeve 104 is removed from outer sleeve 102 during a medical procedure. In another embodiment, after using pilot hole guide portion 118 and pilot hole aperture 120 to drill a pilot hole during a medical procedure, inner sleeve 104 is removed from outer sleeve 102 and soft tissue protection element 106 in conjunction with the drilled pilot hole is used to ream a larger diameter portion of one or more bone elements. In one embodiment, inner diameter of soft tissue protection element 106 varies based on an outer diameter of a bone implant being inserted into bones, and accordingly, the size of pilot hole guide portion 118 would vary proportionally to provide a flush fit of pilot hole guide portion 118 within soft tissue protection element 106.

Inner sleeve 104 and outer sleeve 102 of stabilization apparatus 100 may comprise an interlocking mechanical device, such as interlocking inner sleeve handle 122 and interlocking outer sleeve handle 112, respectively. Interlocking inner sleeve handle 122 may comprise mechanical stop 124 which corresponds to a mechanical stop 114 of interlocking outer sleeve handle 112 to limit rotation of interlocking inner sleeve handle 122 and interlocking outer sleeve handle 112 relative to one another, thus defining a locking position. Interlocking inner sleeve handle 122 may also comprise, or may instead comprise, a mechanical stop 126, for example an overlay portion, which corresponds to a mechanical stop 116, for example an underlay portion, to limit removal of inner sleeve 104 from outer sleeve 102 when in a locking position.

Any of outer sleeve 102, inner sleeve 104, and support rods 110 may comprise any of a variety of materials, including one or more of a metal, an alloy, a composite, a polymer, or another organic material or biocompatible material. In one embodiment, any of outer sleeve 102, inner sleeve 104, and support rods 110 comprises a radio translucent (radiolucent) material, a non-radio translucent (non-radiolucent) material, or a combination of a radiolucent material and a non-radiolucent material. Outer sleeve 102 and/or soft tissue protection element may comprise a substantially resilient material configured to minimize the effect of its contact with soft tissues.

In one embodiment, stabilization apparatus 100 may be used for placement of an initial pilot hole into bone elements to be fixated, while protecting soft tissues as well as maintaining the position of the bone elements and guiding a ream during a reaming of one or more bone elements to accept an orthopedic implanted device.

In one embodiment, outer sleeve 102 comprises a bore extending substantially centrally through outer sleeve 102. This bore may be configured to guide a reamer during reaming. This bore may be configured to guide an orthopedic implant during implantation in a patient's body.

Figure 2:
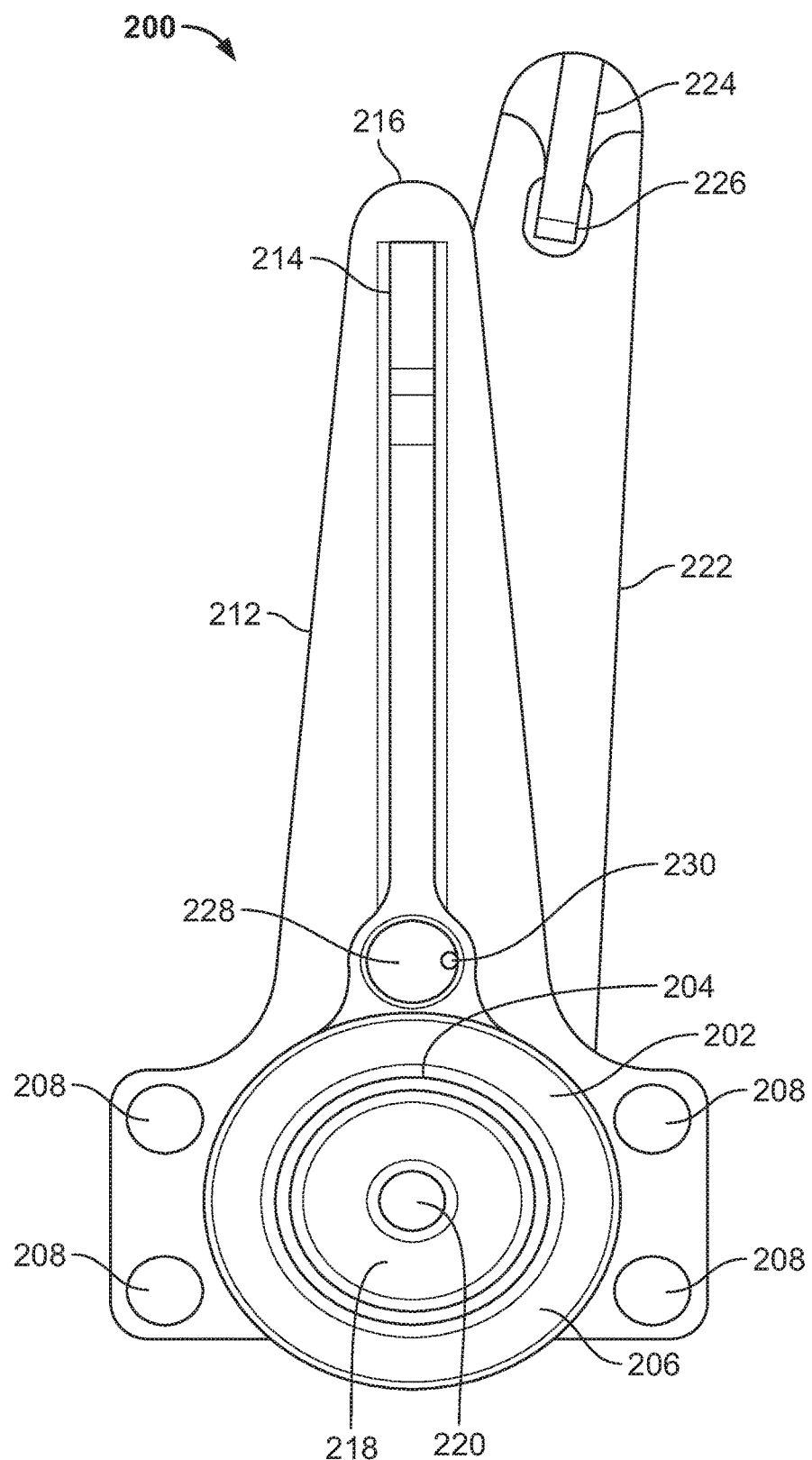
FIG. 2 illustrates an anterior view of an example arrangement of a stabilization apparatus.

FIG. 2 illustrates an anterior view of stabilization apparatus 200. Stabilization apparatus 200 may comprise outer sleeve 202, and inner sleeve 204. Pilot hole guide portion 218 with pilot hole 220 of inner sleeve 204 may couple with soft tissue protection element 206 of outer sleeve 202 to join portions 202 and 204. Portions 202 and 204 may be interlocked by means of mechanical stops 214, 216, 224, and 226 or other like interlocking mechanical device disposed on handles 212 and 222 respectively. In addition to mechanical stops 214, 216, 224, and 226 to interlock both handles, outer sleeve handle 212 may contain movement limiting insert 228 which corresponds to detent 230 on inner sleeve handle 222. Movement limiting insert 228 allows for an insertion of a movement limiting device such a spring loaded ball bearing, pin, or other like device to interact with and frictionally engage detent 230 to limit rotational movement of outer sleeve 202 relative to inner sleeve 204 to keep the two portions locked. Support rod apertures 208 are disposed about soft tissue protection element 206 on outer sleeve 202.

Figure 3:
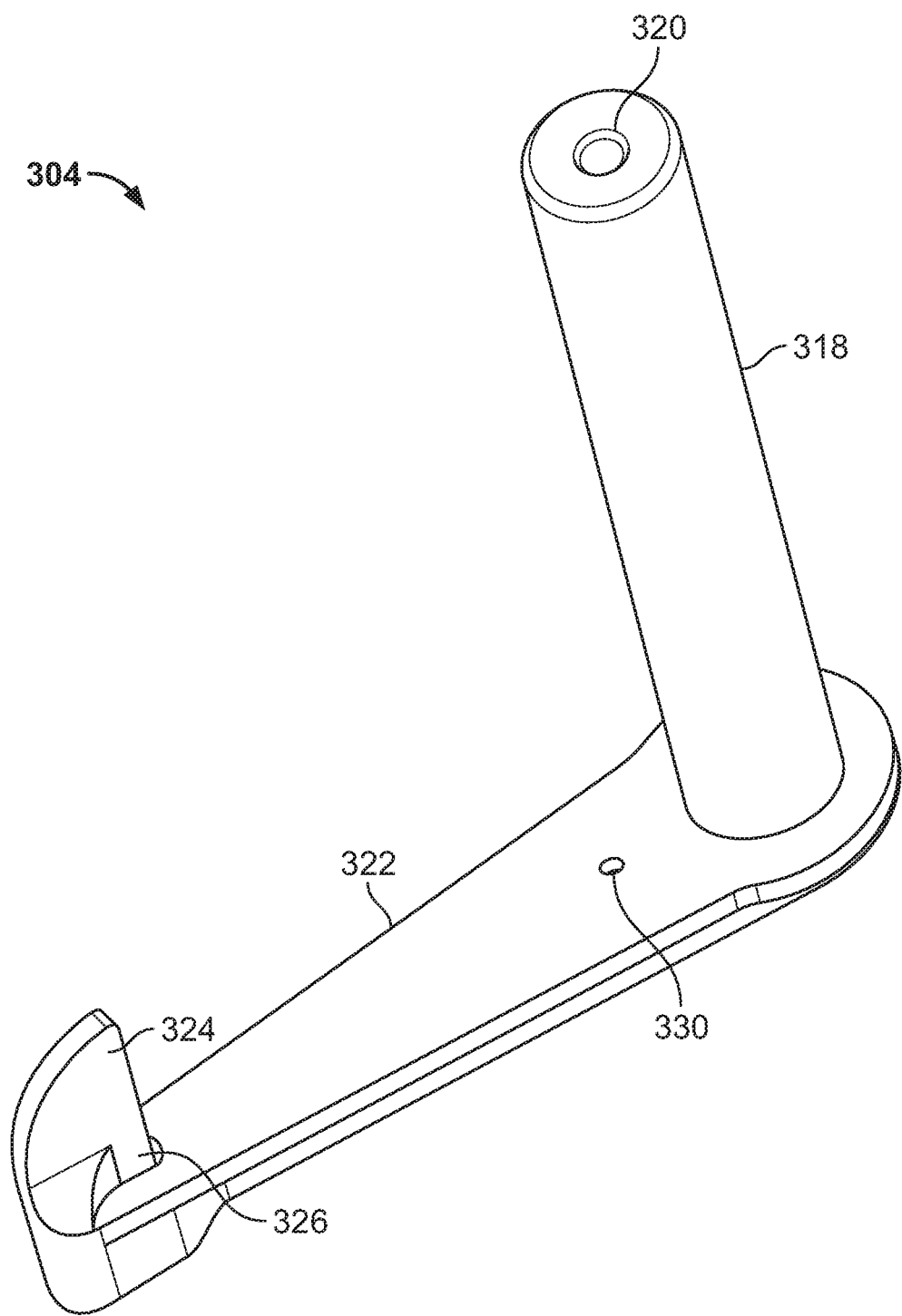
FIG. 3 illustrates an example arrangement of an inner sleeve of a stabilization apparatus.

FIG. 3 illustrates an example embodiment of inner sleeve 304. Inner sleeve 304 may comprise a handle 322 on which is disposed a pilot hole guide portion 318 with pilot hole aperture 320 for use in drilling a pilot hole in one or more bone elements during a medical procedure, and mechanical stops 324, 326, and detent 330 used to interact with other mechanical devices to limit rotational movement of handle 322 during a medical procedure.

Figure 4:
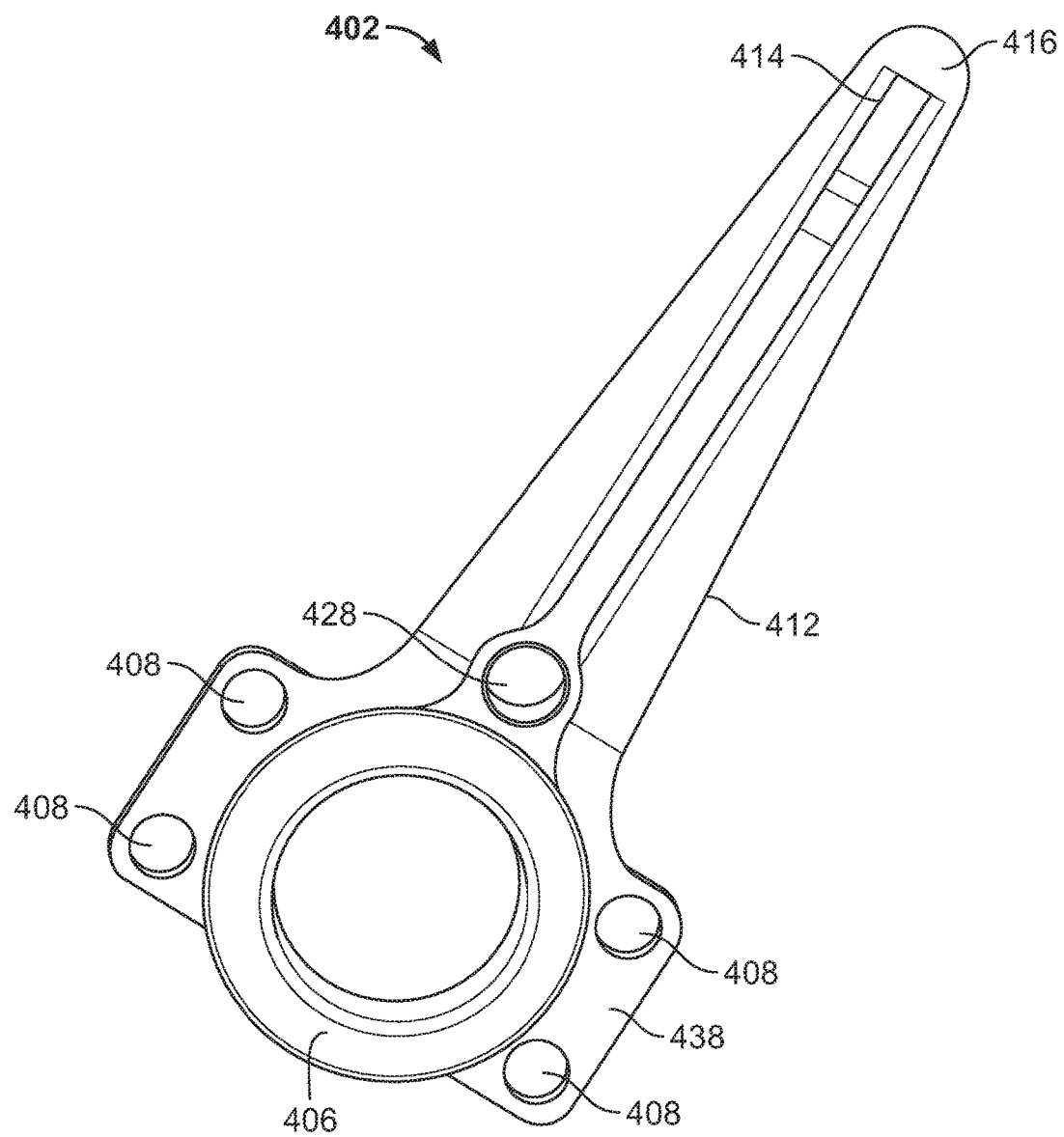
FIG. 4 illustrates an example arrangement of an outer sleeve of a stabilization apparatus.

FIG. 4 illustrates an example embodiment of outer sleeve 402. Outer sleeve 402 may comprise a handle 412 on which is disposed a soft tissue protection element 406 for protecting soft tissue during a medical procedure and further operable to guide a bone element reamer, support rod aperture offsets 438 disposed around soft tissue protection element 406, support rod aperture offsets comprising one or more apertures 408 for receiving and guiding a support rod during a medical procedure, and mechanical stops 414, 416, and movement limiting insert 428 used to interact with other mechanical devices to limit rotational movement of handle 412 during a medical procedure.

Figure 5:
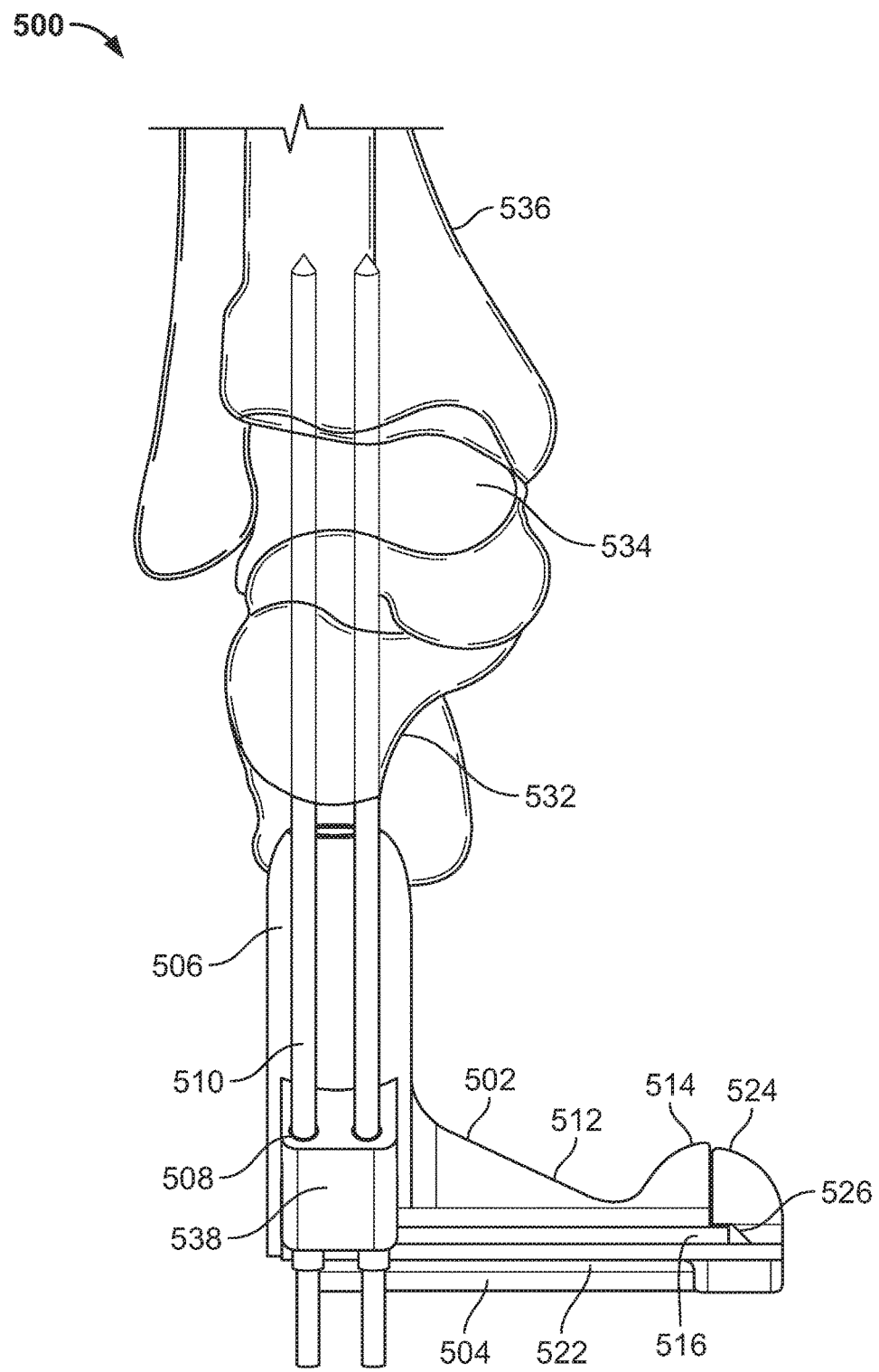
FIG. 5 illustrates an example arrangement of a stabilization apparatus in use.

FIG. 5 illustrates an example embodiment of stabilization apparatus 500 used during an example medical procedure. Stabilization apparatus 500 may be secured relative to one or more bones during a medical procedure. In this example embodiment, stabilization apparatus is secured to calcaneus bone 532, talus bone 534, and tibia bone 536. Stabilization apparatus may be secured to bones 532, 534, and 536 by first excising soft tissue for an area of the body an inserting soft tissue protection element 506 into the soft tissue. One or more support rods 510 are guided through support rod apertures 508 on support rod aperture offset 538 to interact with bones 532, 534, and 536 to secure stabilization apparatus 500 relative to bones 532, 534, and 536. Pilot hole guide portion (not shown) and pilot hole aperture (not shown) of inner sleeve 504 are used to guide a pilot hole through bones 532, 534, and 536. Handle 522 is rotated relative to handle 512 to disengage mechanical stops 514, 516, 524, and 526 such that inner sleeve 504 may be removed from outer sleeve 502. Once inner sleeve 504 is removed from outer sleeve 502, soft tissue protection element 506 in addition to the drilled pilot hole may be used to guide a larger diameter bone reamer through bones 532, 534, and 536 such that a corresponding diameter bone implant may be inserted into the bore. Soft tissue protection element 506 is left in place for a remainder of the medical procedure to protect the soft tissue during the insertion of the bone implant. Alternatively, soft tissue protection element 506 is removed after reaming.

Figure 6:
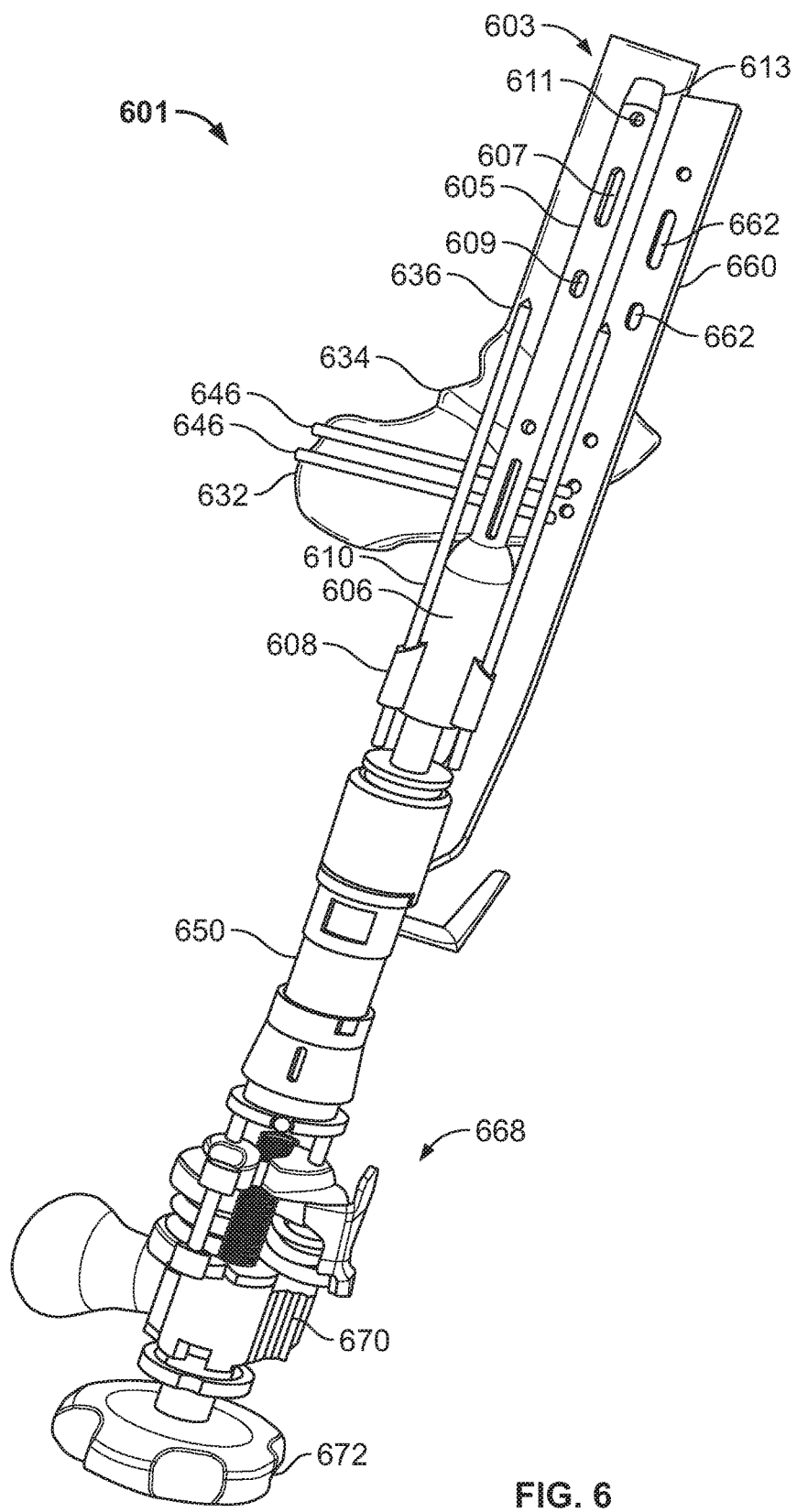
FIG. 6 illustrates a system for causing compression of bone elements.

FIG. 6 illustrates an example arrangement of a system 601 for causing compression between bone elements as used in a medical procedure fusing ankle bones 632, 634, and 636. FIG. 6 illustrates a medial view of bones 632, 634, and 636 within a human left foot. System 601 may include bone implant apparatus 603 for causing compression between bone elements in addition to targeting arm 660, soft tissue protective sleeve 606 of stabilization apparatus 600, and tensioning device 668.

In an example embodiment, an apparatus 603 for causing compression between bone elements is inserted into bones 632, 634, and 636. Before insertion of apparatus 603, soft tissue protection element 606 is used to prepare bones 632, 634, and 636 for insertion. Soft tissue on the bottom of the foot proximate to calcaneus 632 is excised to allow for at least partial insertion of soft tissue protection element 606 into the soft tissue proximate to calcaneus 632. Soft tissue protection element 606 further comprises an inner sleeve (not shown) which fits into and is removable from soft tissue protection element 606. After insertion of soft tissue protection element 606 into the soft tissue at the bottom of the foot, one or more support rods 610 are inserted into support rod alignment apertures 608 on soft tissue protection element 606. Support rods 610 are drilled into bones 632, 634, and 636 to hold soft tissue protection element 606 in place within the soft tissue and relative to bones 632, 634, and 636. An inner sleeve with a central guide for drilling a pilot hole is inserted into soft tissue protection element 606. A pilot hole is drilled through bones 632, 634, and 636 and inner sleeve is removed from soft tissue protection element 606. Inner-diameter of soft tissue protection element 606 is sized accordingly to match an outer diameter of apparatus 603. Using the drilled pilot hole as a guide, soft tissue protection element 606 is used as a guide to ream the full outer diameter of apparatus 603 from bones 632, 634, and 636. Accordingly, inner diameter of soft tissue protection element 606 may vary based on the outer diameter size of apparatus 603 to be inserted, and inner sleeve diameter will vary accordingly to ensure a proper fit between inner sleeve and soft tissue protection element 606. Soft tissue protection element 606 protects surrounding soft tissue during the drilling and reaming of bones 632, 634, and 636. After bones are reamed to the appropriate diameter, targeting arm 662 is used to drill apertures through bones 632, 634, and 636. Referring to system 601 targeting arm 660, targeting arm 660 has multiple apertures 662 corresponding to apertures of compression slot 607, dynamization slot 609, and static fixation apertures 611 on apparatus 603. Targeting arm 660 is used as a guide to drill apertures corresponding to compression slot 607, dynamization slot 609, and static fixation apertures 611 through bones 632, 634, and 636. Target arm 660 rotates in intervals of 90 degrees to match the 90 degree offset of apertures corresponding to compression slot 607, dynamization slot 609, and static fixation apertures 611 on apparatus 603 such that apertures drilled through bones 632, 634, and 636 will match precisely with those apertures of compression slot 607, dynamization slot 609, and static fixation apertures 611 on apparatus 603 once apparatus 603 is inserted into bones 632, 634, and 636. After apertures are drilled through bones 632, 634, and 636, distal end 820 of elongated shaft 602 is inserted through soft tissue protection element 606 and through 632, 634, and 636 until proper alignment of apparatus 603 relative to the drilled bone apertures is achieved. Nail fastener (not shown) may be used to manipulate apparatus 603 to achieve proper alignment within the body. Once apparatus 603 is aligned, calcaneal screws 646 are inserted through calcaneus 632 and through corresponding static fixation apertures on apparatus 603 to partially, statically fix apparatus 603 relative to bones 632, 634, and 636. A transverse bolt is inserted through the corresponding drilled aperture in tibia 636 for compression slot 607 and through compression slot 607. A cable, not shown, within an inner longitudinal bore of apparatus 603 is positioned appropriately to interact with the transverse bolt through compression slot 607. Cable ends (not shown) pass through support device 650 and further to tensioning device 668 and portions of the cable are secured to cable securing cams 670 of tensioning device 668. Cables may be tensioned by twisting ratcheting tension adjustment 672 which incrementally increases tension to the cable, and thus the tension between the cable and transverse bolt through compression slot 607. As the cable is tensioned, bones 632, 634, and 636 and their respective joints are drawn to each other until a proper tensioning has been achieved. Once a proper tensioning is achieve, more transverse bolts are secured through the drilled apertures on bones 632, 634, and 636 and through apertures corresponding to dynamization slot 609, and static fixation apertures 611 of apparatus 603 to provide a final fixation of apparatus 603 within bones 632, 634, and 636. After apparatus 603 has been finally fixated, cams 670 are released to slacken the cable, and tensioning device 668 is removed from system 601. Cable is remove from apparatus 603 via apertures (not shown) on support device 650. Support device 650 and its corresponding portion within soft tissue protection element 606 are removed in addition to the nail fastener. Targeting arm 660 is removed to leave soft tissue protection element 606 as anchored in place. Support rods 610 may either remain within the body or be removed with soft tissue protection element 606 and the soft tissue left after removal of soft tissue protection element 606 is closed to complete this example embodiment of a bone compression and fixation procedure. Accordingly, other procedures and steps may be used to effectuate this example embodiment and the example embodiment was used to illustrate use of apparatus 603 relative to system 601 for a compression between bone elements medical procedure.

Figure 7:
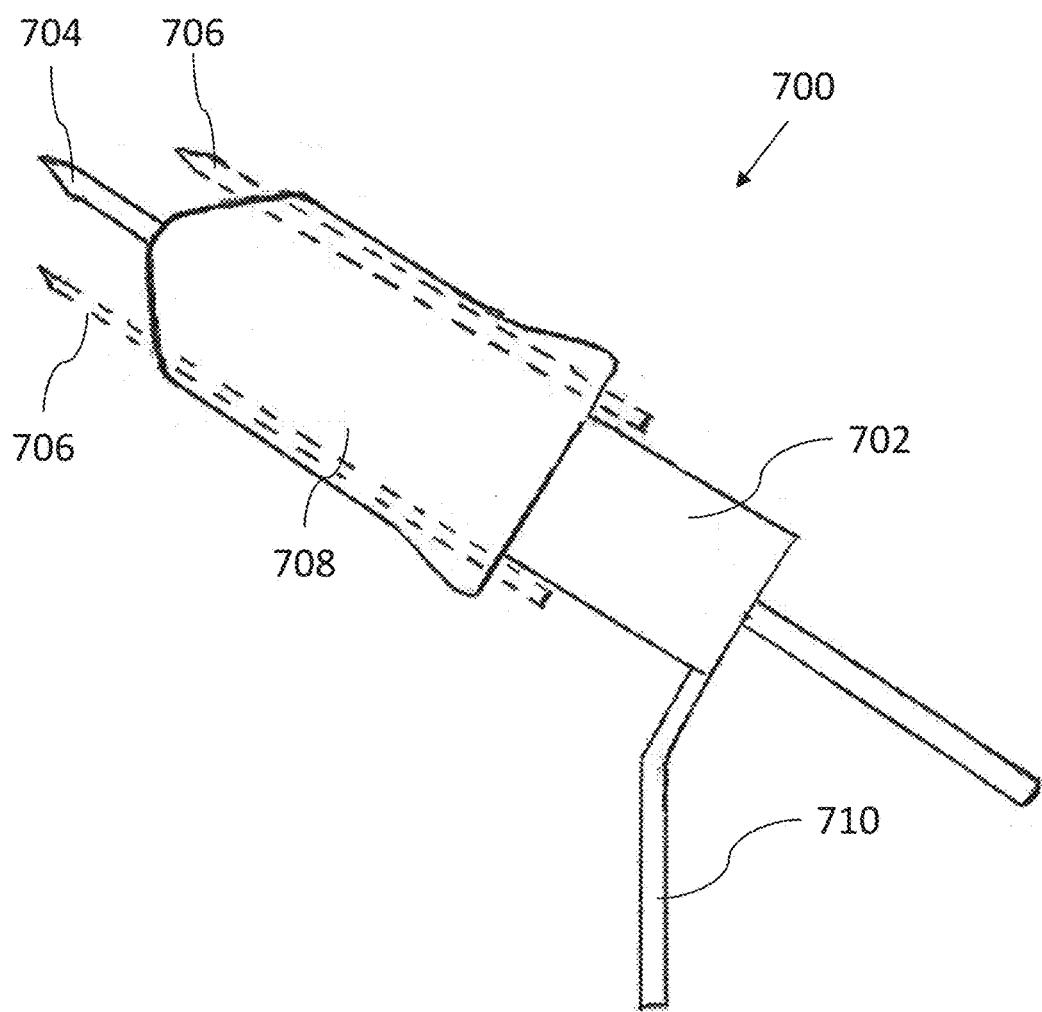
FIG. 7 illustrates an example arrangement of a stabilization apparatus.

FIG. 7 illustrates an example arrangement of a stabilization apparatus 700. Stabilization apparatus 700 may comprise an outer sleeve 702 through which a guide wire 704 and support rod 706 may extend. Stabilization apparatus 700 may also comprise a blunt tip soft tissue protection element 708 and handle 710. In one embodiment, the term "outer sleeve" may be interchangeable with the term "body portion." In another embodiment, the term "support rod" may be interchangeable with "stabilizing wires" or "stabilization wires." In another embodiment, the term "soft tissue protection element" may be interchangeable with the term "outer sleeve." In another embodiment, the term "handle" may be interchangeable with the term "mounting portion."

Stabilization apparatus 700 may be configured to maintain one or more bone elements in a specific desired orientation for reaming a hole through the one or more bone elements. Stabilization apparatus 700 may be configured to maintain one or more bone elements in a specific desired orientation for implantation of an orthopedic implanted device through one or more bone elements. In one embodiment, stabilization apparatus 700 is configured to maintain one or more joints in a specific desired orientation for reaming a hole through the one or more bone elements making up the joint, for insertion of an apparatus for causing compression between bone elements.

Outer sleeve 702 may comprise a substantially cylindrical profile with a series of apertures extending longitudinally through the body of outer sleeve 702. The apertures may permit the passing of any of guide wire 704 or support rod 706 through outer sleeve 702. The aperture for guide wire 704 may be substantially centrally located within outer sleeve 702.

The apertures for support rod 706 may be offset to either side of outer sleeve 702. In one embodiment, the apertures for support rod 706 may be substantially opposed, and oriented about 180 degrees relative to the aperture for guide wire 704. In another embodiment, stabilization apparatus 700 comprises three or more apertures for support rod 706, which apertures may be substantially evenly distributed about the periphery of outer sleeve 702. That is, three apertures may be oriented about 120 degrees relative to the aperture for guide wire 704, while four apertures may be oriented about 90 degrees relative to the aperture for guide wire 704, and so on.

In one embodiment, one or more of guide wire 704 and support rod 706 comprise a cutting tip configured to create a channel through bone elements upon rotation of guide wire 704 or support rod 706. In another embodiment, one or more of guide wire 104 and support rod 706 are configured to be inserted following the drilling of a channel through bone elements with a drill bit. In another embodiment, one or more of guide wire 704 and support rod 706 comprise a pointed tip configured to create a channel through bone elements upon being driven with an axial force.

Soft tissue protection element 708 may be oriented radially outwardly of outer sleeve 702. Soft tissue protection element 708 may be configured to provide protection of soft tissues adjacent to or surrounding the site of bone elements to be reamed. For example, soft tissue protection element 708 may protect skin, muscle, and ligament from contacting or being damaged by any of guide wire 704, support rod 706, or outer sleeve 702 during use of stabilization apparatus 700.

Handle 710 may comprise any of a variety of devices configured to maintain control of stabilization apparatus 700 by a user, including a handle or tab for holding in a user's hand or selectively connecting to an anchoring device configured to provide stability to stabilization apparatus 700 relative to the patient or the patient's bone elements.

Any of outer sleeve 702, guide wire 704, support rod 706, soft tissue protection element 708, and handle 710 may comprise any of a variety of materials, including one or more of a metal, an alloy, a composite, a polymer, or another organic material or biocompatible material. In one embodiment, any of outer sleeve 702, guide wire 704, support rod 706, soft tissue protection element 708, and handle 710 comprises a radiolucent material, a non-radiolucent material, or a combination of a radiolucent material and a non-radiolucent material. Soft tissue protection element 708 may comprise a substantially resilient material configured to minimize the effect of its contact with soft tissues.

In one embodiment, stabilization apparatus 700 may be used for placement of an initial guide wire into bone elements to be fixated, while protecting soft tissues as well as maintaining the position of the bone elements during placement of a longitudinal bore to accept an orthopedic implanted device.

Figure 8:
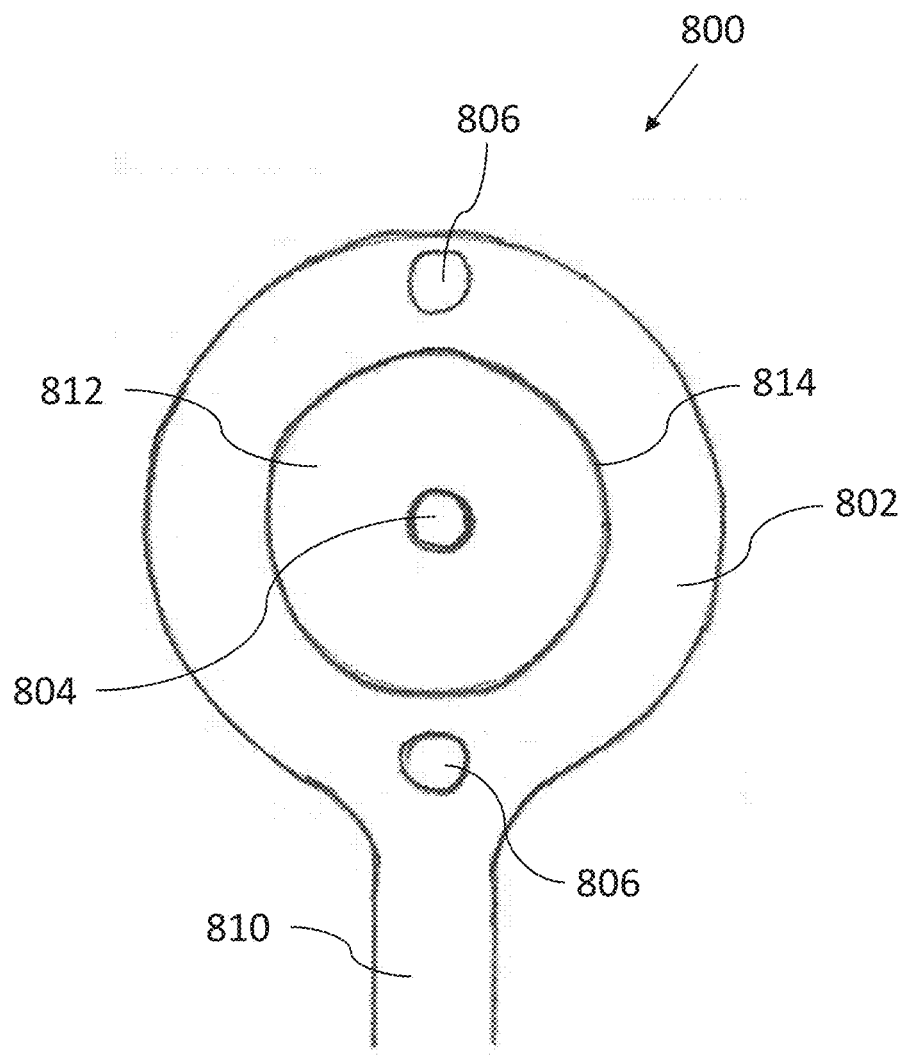
FIG. 8 illustrates an example arrangement of a stabilization apparatus.

FIG. 8 illustrates an end view of an example arrangement of a stabilization apparatus 800 comprising an outer sleeve 802, a pilot hole aperture 804, one or more support rod apertures 806, a handle 810, and an inner sleeve 812. In one embodiment, the term "pilot hole aperture" may be interchangeable with the term "guide wire aperture." In another embodiment, the term "inner sleeve" may be interchangeable with the term "removable insert."

Stabilization apparatus 800 may be configured substantially similar to stabilization apparatus 700 illustrated in FIG. 7.

Inner sleeve 812 may comprise a substantially cylindrical body including pilot hole aperture 804 and configured to fit within a bore 814 of stabilization apparatus 800. Inner sleeve 812 may comprise any of a variety of materials, including one or more of a metal, an alloy, a composite, a polymer, or another organic material or biocompatible material. In one embodiment, inner sleeve 812 comprises at least one of a radiolucent material, a non-radiolucent material, or a combination of a radiolucent material and a non-radiolucent material.

In one embodiment, inner sleeve 812 may comprise a series of removable inserts, each with larger pilot hole apertures 804 extending longitudinally through their length. In use, stabilization apparatus 800 may be loaded with a first inner sleeve 812 having a pilot hole aperture 804 configured to accept a guide wire fitted with a cutting head. Following the reaming of bone elements with a guide wire, the guide wire and first inner sleeve 812 may be removed. A second inner sleeve 812 including a larger pilot hole aperture 804 may be inserted into stabilization apparatus 800, after which a guide wire having a greater diameter than that used with first inner sleeve 812 may be extended through second inner sleeve 812. In one embodiment, a third inner sleeve 812 with a larger pilot hole aperture 804 may replace the second inner sleeve 812, and so on.

In one embodiment, bore 814 comprises about the same diameter as the outside diameter of the orthopedic implanted device to be implanted. A reamer having an outside diameter about the same diameter as bore 814 may be extended through stabilization apparatus 800 and the bone elements to be fixated, and removed. The orthopedic implanted device may be inserted through bore 814 of stabilization apparatus 800 and through the bone elements to be fixated. Upon placement of the orthopedic implanted device, stabilization apparatus 800 may be removed, leaving the orthopedic implanted device installed within the bone elements.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A stabilization apparatus for reaming bone elements, the stabilization apparatus comprising:
    an outer sleeve having support rod apertures and a transversely extending handle;
    support rods configured to extend through the support rod apertures and into one or more bone elements to secure the outer sleeve to the bone elements;
    an inner sleeve having a transversely extending handle and being configured for movement axially into and out of the outer sleeve, and for movement rotationally relative to the outer sleeve, including movement axially and rotationally into and out of a locking position in which the handles have overlapping portions, when the outer sleeve is secured to the bone elements by the support rods; and
    means for releasably blocking movement of the inner sleeve axially out of the outer sleeve, and means for simultaneously blocking rotation of the inner sleeve relative to the outer sleeve, when the outer sleeve is secured to the bone elements by the support rods and the inner sleeve is in the locking position;
    wherein the overlapping portions of the handles together are configured to define the blocking means.

2. The stabilization apparatus of claim 1, wherein the outer sleeve comprises a soft tissue protection element for operatively protecting soft tissue during a medical procedure.

3. The stabilization apparatus of claim 1, wherein the outer sleeve is configured to guide a reamer.

4. The stabilization apparatus of claim 1, wherein the support rod apertures include a pair of apertures in positions offset from one another 180 degrees about the outer sleeve.

5. The stabilization apparatus of claim 1, wherein the inner sleeve has a pilot hole guide portion for drilling a pilot hole during a medical procedure.

6. The stabilization apparatus of claim 1, wherein the outer sleeve has a bore extending substantially centrally through the outer sleeve.

7. The stabilization apparatus of claim 1, wherein at least one of the outer sleeve and the inner sleeve comprises at least one of: a radiolucent material or a combination of a radiolucent material and a non-radiolucent material.

8. The stabilization apparatus of claim 1, wherein the support rod apertures include apertures arranged in multiple pairs in which the apertures in each pair are offset from one another 180 degrees about the outer sleeve.

9. The stabilization apparatus of claim 1, wherein the support rod apertures include pairs of apertures that are offset from one another evenly about the outer sleeve.

10. The stabilization apparatus of claim 1, wherein the means for releasably blocking movement of the inner sleeve axially out of the outer sleeve includes an underlay part of one of the handles and an overlay part of the other of the handles.

11. The stabilization apparatus of claim 1, wherein the means for releasably blocking rotation of the inner sleeve relative to the outer sleeve comprises a detent and recess formed by the handles.

12. The stabilization apparatus of claim 1, wherein the overlapping portions of the handles include opposite end portions of the handles.

13. The stabilization apparatus of claim 12, wherein the opposite end portions of the handles include free outer end portions defining the means for releasably blocking movement of the inner sleeve axially out of the outer sleeve.

14. The stabilization apparatus of claim 12, wherein the overlapping portions of the handles include inner end portions defining the means for blocking rotation of the inner sleeve relative to the outer sleeve.

* * * * *